United States Patent
Baluch

(10) Patent No.: US 6,498,286 B1
(45) Date of Patent: Dec. 24, 2002

(54) GERMPLASM CONTAINING AN IDENTIFIER NUCLEOTIDE SEQUENCE AND METHOD FOR IDENTIFYING GERMPLASM

(75) Inventor: Stephen J. Baluch, Lafayette, IN (US)

(73) Assignee: FFR Cooperative, Battle Ground, IN (US)

( * ) Notice: Subject to any disclaimer, the term of this patent is extended or adjusted under 35 U.S.C. 154(b) by 0 days.

(21) Appl. No.: 09/137,130

(22) Filed: Aug. 20, 1998

(51) Int. Cl.$^7$ .............. A01H 5/00; A01H 1/00; A01H 1/04; C12Q 1/68
(52) U.S. Cl. .............. 800/300; 800/312; 800/260; 800/320.3; 435/6; 435/91.1; 435/91.2; 435/440; 435/468
(58) Field of Search ................ 800/312, 300, 800/260, 320.3; 435/6, 91.1, 91.2, 440, 468

(56) References Cited

U.S. PATENT DOCUMENTS

| | | |
|---|---|---|
| 4,717,653 A | 1/1988 | Webster, Jr. ............... 435/5 |
| 5,087,558 A | 2/1992 | Webster, Jr. ............... 435/5 |
| 5,451,513 A | 9/1995 | Maliga et al. ............ 435/172.3 |
| 5,545,817 A | 8/1996 | McBride et al. ............ 800/205 |
| 5,545,818 A | 8/1996 | McBride et al. ............ 800/205 |
| 5,576,198 A | 11/1996 | McBride et al. ............ 435/91.3 |
| 5,614,361 A | 3/1997 | Webster, Jr. ............... 435/5 |
| 5,645,990 A | 7/1997 | Love ........................ 435/6 |
| 5,652,128 A | 7/1997 | Jarvik ..................... 435/172.3 |
| 5,674,687 A | 10/1997 | Hershfield ................ 435/6 |
| 5,936,142 A | * 8/1999 | Steiger et al. ............ 800/312 |
| 6,084,155 A | * 7/2000 | Volrath et al. ............ 800/300 |

OTHER PUBLICATIONS

Bilang, Roland, and Potrykus, Ingo, *Containing excitement over transplastomatic plants*, Apr. 16, 1998, pp. 333–334, Nature Biotechnology vol. 16.

Daniell, Henry; Datta, Rina; Varma, Sam; Gray, Steven; and Lee, Seung–Bum, *Containment of herbicide resistance through genetic engineering of the chloroplast genome*, Apr. 16, 1998, pp. 345–348, Nature Biotechnology vol. 16.

Korab–Laskowska, M.; Rioux, P; Brossard, N.; Littlejohn, T.G.; Gray, M.W.; Lang, B.F.; Burger, G., *The Organelle Genome Database Project (GOBASE)*, Jan. 1, 1998, pp. 138–144,, Nu cleic Acids Res. (Abstract).

Provan, J.; Corbett, G.; Waugh, R.; McNicol, J.W.; Morgante, M.; Powell, W.; *DNA fingerprints of rice (Oryza sativa) obtained from hypervariable chloroplast simple sequence repeats*, Oct. 22, 1996, pp. 1275–1281, Proc. R. Soc. Lond. B. Biol. Sci. (Abstract).

Johnston, Stephen A.; Anziano, Paul Q.; Shark, Kathy; Sanford, John C.; and Butow, Ronald A., *Mitochondrial Transformation in Yeast by Bombardment with Microprojectiles*, Jun. 10, 1988, pp. 1538–1541, Science vol. 240.

Fox, T.D.; Sanford, J.C.; McMullin, T.W., *Plasmids can stably transform yeast mitochondria lacking endogenous mtDNA*, Oct., 1988, pp. 7288–7292, Proc. Natl. Acad. Sci. USA (Abstract).

* cited by examiner

*Primary Examiner*—Jezia Riley
(74) *Attorney, Agent, or Firm*—Rothwell, Figg, Ernst & Manbeck PC

(57) ABSTRACT

The present invention is directed to germplasm containing an identifier nucleotide sequence and to a method for identifying germplasm, more particularly the source of germplasm. The present invention is especially useful for determining the ownership of germplasm, plant or animal. Briefly, the invention is directed to the production of transgenic organisms which contain an identifier nucleotide sequence within the organellar genome. The identifier nucleotide sequence is selected such that it is capable of indicating the source of the germplasm. The organellar genome of germplasm to be tested is isolated and analyzed for the presence of the identifier nucleotide sequence. The presence of the identifier nucleotide sequence establishes the source of the germplasm.

6 Claims, No Drawings

GERMPLASM CONTAINING AN IDENTIFIER NUCLEOTIDE SEQUENCE AND METHOD FOR IDENTIFYING GERMPLASM

BACKGROUND OF THE INVENTION

The present invention is directed to germplasm containing an identifier nucleotide sequence and to a method for identifying germplasm, more particularly the source of germplasm. The present invention is especially useful for determining the ownership of germplasm, including plants and animals, or the ownership of germplasm used as a parent in the development of germplasm. Briefly, the invention is directed to the production of transgenic organisms which contain an identifier nucleotide sequence within the organellar genome, including but not limited to plastids and mitochondria. The identifier nucleotide sequence is selected such that it is capable of indicating the source of the germplasm. The organellar genome of germplasm to be tested is isolated and analyzed for the presence of the identifier nucleotide sequence. The presence of the identifier nucleotide sequence establishes the source of the germplasm.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The classification of organisms has traditionally been done along more or less arbitrary and some-what artificial lines. For example, the living world has been divided into two kingdoms, namely plants and animals. This classification works well for generally familiar organsims, but becomes more difficult for such organisms as unicellular ones. Where classification of organisms becomes more than a scientific exercise is in the identification of plants and animals for hybridization and breeding programs, and in accurate and reliable identification of microorganisms which may infect plants and animals. For example, the plant breeder may wish to have a quick and reliable means of identifying different species and strains for use in their breeding programs. In addition, the owner of a particular plant variety may wish to have a quick and reliable means of identifying his variety for establishing derivation or ownership of germplasm. Thus, the correct identification of species or varieties of organisms is of particular importance.

Biological samples have been collected and analyzed for a variety of reasons relating to agricultural forensic, e.g., to identify individuals for population genetics or variety derivation. The known methods of analyzing biological samples from plants include using the proteins, specific enzymes or the nucleic acids to identify individually specific patterns within a species. For example, protein from a plant can be isolated and subjected to a two-dimensional electrophoretic analysis to produce a protein fingerprint (Anderson et al., 1985; Choi et al., 1984). Alternatively, isozymes, i.e., specific enzymes which exist in several forms in plants, can be isolated and subjected to electophoresis to produce an isozyme fingerprint (Nielsen, 1985; Shields et al., 1983). Finally, the nucleic acids can be isolated and analyzed to produce a DNA fingerprint (U.S. Pat. No. 5,674,687; U.S. Pat. No. 4,963,663; Helentjaris et al., 1985; Landry et al., 1985; Jeffreys et al., 1985). DNA fingerprinting has utilized restriction fragment length polymorphisms and the use of minisatellite and microsatellite probes and/or amplification primers to obtain highly specific patterns which are useful to identify individuals within a known species or in pedigree studies to determine lineage. DNA fingerprinting is generally useful for identifying individuals because it uses patterns that are individually-specific and complex. Similarly, two-dimensional protein fingerprint could be used to identify individuals on the basis of complex patterns. An isozyme fingerprint is less complex but also has less resolution power.

Although each of these methods or a combination of these methods can be used to identify individuals, they have several disadvantages including: (a) time-consuming, (b) complex, sometimes with many steps, (c) requiring skilled and knowledgeable technicians, (d) non-standardization with results varying from lab to lab and test to test and (e) inaccurate measurements often with subjective interpretation. Thus, there is a definite need for a method to identify the source or parentage of germplasm which is easy to perform, relatively fast, does not require significant expertise and requires no subjectivity of interpretation. The present invention solves this need as illustrated herein.

SUMMARY OF THE INVENTION

The present invention is directed to germplasm containing an identifier nucleotide sequence and to a method for identifying germplasm, more particularly the source or parentage of germplasm. The present invention is especially useful for determining the ownership of germplasm, including plants and animals, or the ownership of germplasm used as a parent in the development of germplasm. Briefly, the invention is directed to the production of transgenic organisms which contain an identifier nucleotide sequence within the organellar genome. The identifier nucleotide sequence is selected such that it is capable of indicating the source of the germplasm. The organellar genome of germplasm to be tested is isolated and analyzed for the presence of the identifier nucleotide sequence. The presence of the identifier nucleotide sequence establishes the source or parentage of the tested germplasm.

DETAILED DESCRIPTION OF THE INVENTION

The present invention avoids the problems of prior art fingerprinting techniques for the identification of the source of germplasm. The present invention is simpler and easier to use than prior art fingerprinting techniques and requires no subjective interpretation of the results of the method.

The present invention is directed to germplasm containing an identifier nucleotide sequence and to a method for identifying germplasm, more particularly the source or parentage of germplasm. The present invention is especially useful for determining the ownership of germplasm, including plants and animals, or the ownership of germplasm used as a parent in the development of germplasm. Briefly, the invention is directed to the production of transgenic organisms which contain an identifier nucleotide sequence within the organellar genome. The identifier nucleotide sequence is selected such that it is capable of indicating the source of the germplasm. The organellar genome of germplasm to be tested is isolated and analyzed for the presence of the identifier nucleotide sequence. The presence of the identifier nucleotide sequence establishes the source or parentage of the tested germplasm.

In order to more fully understand the present invention, the following definitions are provided.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, nucleic acid sequence based amplification (3SR or NASBA) and repair chain reaction (RCR). These methods are well known and widely practiced in the art. See, e.g., U.S. Pat. Nos. 4,683,195 and 4,683,202 and Innis et al., 1990 (for PCR); Wu et al., 1989 and EP 320,308A (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify the identifier nucleotide sequence are preferably complementary to, and hybridize specifically to the identifier nucleotide sequence or to regions that flank a target region therein.

"Germplasm" refers to species or variety of a plant or an animal.

"Identifier nucleotide Sequence" refers to a unique nucleic acid which is not present either in the organellar genome(s) or in both the nuclear and organellar genomes. A nucleotide sequence can be determined to be unique by, for example, using it as a probe in a hybridization assay of the organellar DNA or the total DNA of the germplasm of interest. The identifier nucleotide sequence is capable of identifying the source of germplasm.

"Primer" refers to a sequence comprising about 8 or more nucleotides, preferably about 15 or more nucleotides which forms a stable hybrid with its complentary sequence and which can be used to amplify the identifier nucleotide sequence. Primers for an identifier nucleotide sequence may be derived from the sequence of the ends of the identifier nucleotide sequence or the complement thereof or may be derived from the sequence of organellar nucleic acid (or its complement) adjacent to the point of insertion of the identifier nucleotide sequence. If the target sequence contains a sequence identical to that of the probe, the primers may be short, e.g., in the range of about 8–30 base pairs, since the hybrid will be relatively stable under even highly stringent conditions. Of course longer primers, up to 100 base pairs or more, may also be employed which hybridize to the target sequence with the requisite specificity.

"Probe" refers to a polynucleotide which forms a stable hybrid with that of the target sequence, under highly stringent to moderately stringent hybridization and wash conditions. It is preferred that the probes will be perfectly complementary to the target sequence, such that high stringency conditions will be used. Hybridization stringency may be lessened if some mismatching is used, for example, if a probe which is not completely complementary is utilized. Conditions are chosen which rule out nonspecific/ adventitious bindings, that is, which minimize noise. (It should be noted that throughout this disclosure, if it is simply stated that "stringent" conditions are used that is meant to be read as "high stringency" conditions are used.)

Probes for an identifier nucleotide sequence may be derived from the sequence of the identifier nucleotide sequence or the complement thereof. The probes may be of any suitable length, which span all or a portion of the identifier nucleotide sequence, and which allow specific hybridization to the region. If the target sequence contains a sequence identical to that of the probe, the probes may be short, e.g., in the range of about 8–30 base pairs, since the hybrid will be relatively stable under even highly stringent conditions. Of course longer probes, up to 100 base pairs or more, may also be employed which hybridize to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

"Progeny" refers to any progeny of a particular variety of germplasm and is intended to include progeny of the same variety as well as progeny resulting from the use of the particular variety in a breeding program.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Substantially complementary to" refers to a probe or primer sequences which hybridize to the sequences provided under stringent hybridization conditions and/or to sequences having sufficient homology with an identifier nucleotide sequence, such that the specific probe or primers hybridize to the sequences to which they are complimentary.

"Target region" refers to a region of the nucleic acid which is amplified and/or detected. The term "target sequence" refers to a sequence with which a probe or primer will form a stable hybrid under desired conditions.

"Transgenic organelle" refers to an organelle which contains an identifier nucleotide seqeunce, preferably incorporated into its genome.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991; Gelvin et al., 1990; Grierson et al., 1984.

In accordance with the present invention an identifier nucleotide sequence is selected which can serve to identify the source of germplasm. Using an identifier nucleotide sequence which is not homologous with DNA of the germplasm, e.g., Zea mays L., permits the detection of the presence of the identifier nucleotide sequence simply and accurately. In one embodiment, the identifier nucleotide sequence is not homologous with the germplasm's organellar DNA. For example, the identifier nucleotide sequence is chosen such that it does not occur naturally in the chloroplast genome. The nucleotide sequence of the chloroplast genome for several plant species is known. See for example, Hiratsuka et al. (1989), Ohyama et al. (1986), Shinozaki et al. (1986), Maier et al. (1995), Wakasugi et al. (1997) and Hallick et al. (1993). The nucleotide sequence of the mitochondrial genome of several species is known. See for example, Janke et al. (1997), Lopez et al. (1996), Unseld et al. (1997), Roe et al. (1985), Gadaleta et al. (1989), Zhou et al. (1995) and Wolff et al. (1994). Additional nucleotide sequences for organelles can be found in the "Organelle Genome Database" (Korab-Laskowska et al., 1998). In a more preferred embodiment, the identifier nucleotide sequence is not homologous with any of the germplasm's DNA, both nuclear and organellar. Thus, in the more preferred embodiment, the identifier nucleotide sequence can be derived from a different organism, e.g. a chicken nucleotide sequence could be selected as the identifier nucleotide sequence for plants. This identifier nucleotide sequence could include the complete or partial sequence (genomic or cDNA) for a gene or could include only the promoter element. Alternatively, the identifier nucleotide sequence can be a synthetic sequence which is designed such that it is not present in the DNA of the germplasm. For example, a synthetic sequence can be prepared which contains codons spelling out the name of the company which owns the germplasm in question. Any nucleotide sequence selected for use in the present invention can be determined to be unique by conventional techniques. For example, the nucleotide sequence, its complement or a part thereof can be used as a probe in a hybridization assay of the organellar DNA or the total DNA of the germplasm of interest. Alternatively, primers for the nucleotide sequence can be used to determine if any nucleic acid is amplified in amplification reactions. Preferably, the identifier nucleotide sequence is selected so that it is not capable of being expressed in the germplasm.

Although naked DNA can be used to transform host cells, it is preferred to use vectors which contain the identifier nucleotide sequence. The vectors may also contain selectable marker sequences under control of appropriate host recognizable promoters for use in selecting transformed cells. Suitable markers and promoters are well known in the art. Alternatively, the presence of the integrated identifier nucleotide sequence can be confirmed by assaying for the presence of the identifier nucleotide sequence in transformed tissue. In a preferred embodiment, the vectors for transferring the identifier nucleotide sequence into the desired organelles, or the identifier nucleotide sequence if it is to be used directly, also contains means for inserting the identifier nucleotide sequence and selectable marker into the organelle. The insertion means preferably comprises regions of homology to the target organellar genome which flank the identifier nucleotide sequence and/or selectable marker sequence. Since it is preferred that the identifier nucleotide sequence not be expressed, the identifier nucleotide sequence does not need to be placed under the control of a promoter.

The identifier nucleotide sequence can be introduced into the host cell by well-known methods, e.g., by injection (see, Kubo et al., 1988), or vectors containing the identifier nucleotide sequence can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome or *Agrobacteium tumefaciens*); and other methods. See generally, Sambrook et al., 1989; Ausubel et al., 1992 and Gelvin et al., 1990. The introduction of the polynucleotides into the host cell or organelles of a host cell by any method known in the art, including, interalia, those described herein will be referred to herein as "transformation." The cells into which have been introduced nucleic acids described above are meant to also include the progeny of such cells. Thus, the present invention contemplates plant or animal organelles containing the identifier nucleotide sequence as well as plants, plant seeds, plant cells, animals or animal cells containing organelles with the identifier nucleotide sequence.

In accordance with the present invention, host cells are transformed such that the identifier nucleotide sequence is integrated into the genome of the host cell's organelles. The transformation of plant plastids with the identifier nucleotide sequence can be carried out as described in U.S. Pat. Nos. 5,451,513; 5,545,817; 5,545,818; and 5,576,198; Svab et al., 1990; Svab and Maliga, 1993; Daniell et al., 1990; and Staub et al., 1992. The transformation of mitochondria can be carried out as described in Johnston et al. (1988) and Fox et al. (1988). It is preferred to use microprojectile bombardment, such as described in these references, for the transformation of plant or animal organelles. Generally, plant tissue is bombarded with particles coated with either the identifier nucleotide sequence or a vector containing the identifier nucleotide sequence. The bombarded tissue is cultured on a cell-division-promoting meda, after which transformed tissue is selected. If a selectable marker is used, transformed tissue is selected by culturing plant tissue on selective media. If a selectable marker is not use, transformed tissue is selected by assaying for the presence of the identifier nucleotide sequence. Plants are then obtained from the transformed tissue. This general procedure is adapted according to the general transformation and regeneration methods which have been developed for a given plant species.

General transformation and regeneration methods are well known in the art for most plant species. Plants which have been transformed and regenerated include the following: corn (U.S. Pat. Nos. 5,484,956; 5,489,520; 5,177,010; 5,641,664; and 5,350,689); soybeans (U.S. Pat. Nos. 5,015,580; 5,416,011; 5,563,055; and 5,024,944); alfalfa (U.S. Pat. Nos. 5,324,646 and 5,736,627; McKersie et al., 1993); sorghum (U.S. Pat. No. 5,723,764); wheat (U.S. Pat. Nos. 5,610,042; 5,631,152; and 5,589,617); rice (U.S. Pat. Nos. 5,679,558 and 5,736,369); oats and barley (U.S. Pat. Nos. 5,723,764 and 5,187,073); rye, millet and triticale (U.S. Pat. No. 5,723,764); orchardgrass (Denchev et al., 1997); tall fescue (Dalton et al., 1995); monocot temperate grasses (Horikawa et al., 1993); red clover (Poerba et al., 1997); white clover (Ealing et al., 1994); subterranean clover (Khan et al., 1996); cotton (U.S. Pat. Nos. 5,004,863; 5,159,135; and 5,597,718); rapeseed (U.S. Pat. Nos. 5,530,192 and 5,188,958); potato (U.S. Pat. Nos. 5,510,523 and 5,589,612); and tomato (U.S. Pat. Nos. 5,569,831 and 5,569,829).

General methods for producing transgenic animals are well known in the art. See for example, U.S. Pat. Nos. 5,476,995; 5,175,385; 5,573,933; 5,489,742; 5,741,957 and 5,589,604.

The cells of the germplasm, plant or animal, produced in accordance with the present invention contain organelles which contain an identifier nucleotide sequence, preferably integrated into the organellar genome. As is well known in the art, organelles are only transferred to future generations through the female parent and are not passed transferred to progeny by pollen or sperm. Thus, organelles containing an identifier nucleotide sequence in accordance with the present invention will only be passed on to offspring by the female parent. The germplasm of the present invention can be used in any conventional manner, for example to produce progeny of the same variety or to produce new varieties in a breeding program. Since the transgenic organelle is transferred by the female parent, it is possible to identify progeny, whether of the same variety or of a new variety, which has been produced using transgenic germplasm containing an identifier nucleotide sequence. Thus, a further embodiment of the present invention is a method to determine the source of new germplasm, i.e., germplasm suspected of being or having been derived from the transgenic germplasm. Consequently, the source or parentage of the tested germplasm with respect to germplasm containing the identifier nucleotide sequence can be established by the present invention.

In order to detect the presence of the identifier nucleotide sequence in germplasm to be tested, e.g. germplasm suspected of being the same variety as the transgenic germplasm or having been derived from the transgenic germplasm, a sample from the suspected germplasm is prepared and analyzed for the presence or absence of the identifier nucleotide sequence. Generally, the sample is prepared so that the total nucleic acid or the nucleic acid of the organelles can be analyzed.

The detection of the identifier nucleotide sequence in the germplasm to be tested can be accomplished by any technique known in the art. Such techniques include, but are not limited to, the use of probes for the identifier nucleotide sequence or the amplification of the identifier nucleotide sequence. Thus, the present invention contemplates the use of both PCR and non-PCR based screening strategies to detect target sequences with a high level of sensitivity. Such screening methods include two-step label amplification methodologies that are well known in the art.

When a probe (an oligonucleotide or an analog such as a methyl phosphonate backbone replacing the normal phosphodiester), is used to detect the presence of the target sequences the biological sample to be analyzed may be treated, if desired, to extract the nucleic acids. If the identifier nucleotide sequence is homologous to nuclear DNA, the organelles are first isolated before the organellar nucleic acid is extracted. If the identifier nucleotide sequence is not homologous to any of the nuclear or organellar DNA, the nucleic acid can be extracted without isolation of the organelles, although their isolation prior to extraction is preferred. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the identifier nucleotide sequence. Therefore, high stringency conditions are desirable in order to prevent false positives. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; U.S. Pat. No. 4,868,105; and in EP 225,807A. For example, a probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Alterantively, the screening method can involve amplification of the relevant identifier nucleotide sequence. The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays (as described above) can achieve over a million-fold increase in copy number through the use of polymerase-driven amplification cycles. The DNA isolated from the suspected germplasm is amplied using conventional techniques which includes automation. The primers for DNA amplification are selected so that only the identifier nucleotide sequence, if present, is amplified. Suitable primers may include unique sequences derived from the 5' and 3' ends of the identifier nucleotide sequence or from unique sequences 5' of and 3' of the identifier nucleotide sequence from the construct used to introduce the identifier nucleotide sequence into the organelles. In addition, combinations of these primers can be used. Once amplified, the resulting nucleic acid can be detected using conventional techniques, including the use of probes, such as described above. Alternatively, the presence of the identifier nucleotide sequence can be determined by identifying the presence of amplified nucleic acid.

Two-step label amplification methodologies are known in the art. These assays work on the principle that a small ligand (such as digoxigenin, biotin, or the like) is attached to a nucleic acid probe capable of specifically binding to the identifier nucleotide sequence.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

The present invention is described by reference to the following Examples, which are offered by way of illustration and are not intended to limit the invention in any manner. Standard techniques well known in the art or the techniques specifically described below were utilized.

EXAMPLE 1

Plastid Transformation Vectors

Constructs and methods for use in transforming the plastids of higher plants are described in Svab et al. (1990), Svab and Maligi (1993) and Staub et al. (1993). See also, U.S. Pat. No. 5,545,818. The complete DNA sequence of the plastid genome of tobacco is reported by Shinozaki et al. (1986). All plastid DNA references in the following description are to the nucleotide number in tobacco.

An identifier nucleotide sequence is prepared by isolating the coding sequence for the chicken type 5 cytoplasmic actin gene. The coding sequence for this gene is shown as SEQ ID NO:1. Since it is desired that this sequence not be expressed in the transgenic plant, the start codon is removed. This sequence is further processed by the addition of a synthetic adaptor containing a BamHl and a Ncol site on the 5' end of the actin coding sequence and the addition of a synthetic adaptor containing a Bglll and Sall sites on the 3' end of the actin coding sequence using conventional techniques.

A plastid transformation vector is used which carries a passenger gene in a Prrn(L)rbcL(S)/Trps expression cassette with polylinker restriction sites. The Prrn(L)rbcL(S) fragments are described in Svab and Maliga (1993). To prevent expression of the chicken actin gene, the Prrn(L)rbcL(S)5'-regulatory region is removed from the expression construct. The plastid transformation vector also carries a selectable spectinomycin resistance gene (aadA) under control of psbA gene expression signals. The plastid transformation vector contains plastid DNA homology regions to direct insertion of foreign genes into the plastid between the trnV gene and the rps12/7 operon.

The plastid transformation vector is digested with Ncol/Sall restriction endonucleases to remove the encoding region in the passenger gene, which is then replaced with a Ncol/Sall fragment containing the chicken actin coding sequence, yielding a vector desingnated pF111. The insertion of the chicken actin coding sequence into the wild-type plastid genome yields transplastomes Nt-pF111.

EXAMPLE 2

Plant Plastid Transformation

Stable transformation of tobacco plastid genomes by particle bombardment is reported in Svab et al. (1990) and Svab and Maliga (1993). The methods described therein may be employed to obtain plants transformed with the plastid expression constructs described herein. Such methods generally involve DNA bombardment of a target host explant, preferably an explant made from a tissue part which is rich in metabolically active plastids, such a green plant tissues including leaves and cotyledons.

Tobacco seeds (*N. tabacum* v. Xanthi N/C) are surface sterilized in a 50% chlorox solution (2.5% sodium hypochlorite) for 20 minutes and rinsed 4 times in sterile water. These are plated asceptically on a 0.2×MS salts media and allowed to germinate. The seedlings are grown on agar solidified MS media with 30 g/l sucrose (Murashige et al., 1962).

Tungsten microprojectiles (1.0 $\mu$M) are coated with plasmid DNA according to Maliga (1993) and used to bombard mature leaves placed abaxial side up on RMOP media; MS salts, 1 mg/l BAP, 0.1 mg/l NAA, 30 g/l sucrose and 0.7% phytagar (Svab et al., 1990) using a Bio-Rad PDS 1000 He system (Sanford et al.). Plasmid pF111 is used as the coating plasmid DNA.

The bombarded tissue is then cultured for apporximately 2 days on a cell division-promoting media, after which the plant tissue is transferred to a selective media containing an inhibitory amount of the particular selective agent. Transformed explants form green shoots in approximately 3–8 weeks. Leaves from these shoots are then subcultured on the same selective media to ensure production and selection of homoplasmic shoots.

EXAMPLE 3

DNA Gel Blot Analyis of Transplastomic Lines

Transformed plants selected for marker aadA marker gene expression are analyzed to determine whether the entire plastid content of the plant has been transformed (homoplastic transformants). Typically, following two rounds of shoot formation and spectinomycin selection, approximately 50% of the transgenic plantlets which are analyzed are homoplastomic, as determined by Southern blot analysis of plastid DNA. Homoplastomic plantlets are selected for further cultivation.

Following a second round of shoot formation and spectinomycin selection, two transplastomic lines for the chicken actin coding sequence construct are obtained, Nt-pF111. These lines are checked for homoplastomy. Southern blot analysis is used to confirm the integration of the identifier nucleotide sequence in the tobacco plastide genome. Preparation, electrophoresis and transfer of DNA to filters is as described by Svab and Maliga (1993).

The complete disappearnce of the 3.3 kb native tobacco BamHl fragment in the Nt-pF111 transformants with a probe covering the region of integration, and the appearance of expected sized bands for the inserted DNA of the chicken actin coding sequence in those transformants establishes that the transformed plants are homoplastomic for the intended identifier nucleotide sequence.

EXAMPLE 4

Analysis of Plant Progeny

DNA is isolated from tobacco plants using conventional techniques. Tobacco plants use in this example are (a) progeny of the transformed tobacco plants of Example 3, (b) progeny of a cross of the transformed tobacco plants of Example 3 with a second tobacco variety, (c) progney of the second tobacco variety and (d) progeny of the original variety used for transformation. The presence of the chicken actin coding sequence is determined by hybridization probing of isolated DNA with a probe derived from the chicken actin coding sequence using conventional hybridization conditions. Alternatively, the presence of the chicken actin coding sequence is determined by amplifying the target sequence with appropriate primers for the chicken actin coding sequence using conventional techniques. In each instance, the presence of the chicken actin coding seqeuence is found in samples from tobacco plants of (a) and (b) but not in samples from tobacco plants of (c) and (d). This example demonstrates that the source or parentage of germplasm can be determined on the basis of organelles containing an identifier nucleotide sequence.

It will be appreciated that the methods and compositions of the instant invention can be incorporated in the form of and a variety of embodiments, only and a few of which are disclosed herein. It will be apparent to the artisan that other embodiments exist and do not depart from the spirit of the invention. Thus, the described embodiments are illustrative and should not be construed as restrictive.

LIST OF REFERENCES

Anand, R. (1992). *Techniques for the Analysis of Complex Genomes*, (Academic Press).
Anderson et al. (1985). *Crop Science* 25:667.
Ausubel, F. M., et al. (1992). *Current Protocols in Molecular Biology*, (J. Wiley and Sons, N.Y.)
Choi et al. (1984). *Plant Mol. Biol. Rept.* 2:19.
Compton, J. (1991). *Nature* 350:91–92.
Dalton, S. J. et al. (1995). *Plant Science* 108:63–70.
Daniell et al. (1990). *Proc. Natl. Acad. Sci. USA* 87:88–92.
Denchev, P. D. et al. (1997). *Plant Cell Reports* 16:813–819.
Ealing et al. (1994). *Transgenic Res.* 3:344–354.
Fahy, E., et al. (1991). *PCR Methods Appl.* 1:25–33.
Fox et al. (1988). *Proc. Nati. Acad. Sci. USA* 85:7288–7292.
Gadaleta, G. et al. (1989). *J. Mol. Evol.* 28:497–516.
Gelvin et al. (1990). *Plant Molecular Biology: Manual* (Kluwer Academic Publishers, Dordrect).
Glover, D. (1985). *DNA Cloning*, I and II (Oxford Press).
Grierson et al. (1984). *Plant Molecular Biology* (Blackie, Glasgow).
Guthrie, G. and Fink, G. R. (1991). *Guide to Yeast Genetics and Molecular Biology* (Academic Press). Hallick, R. B. et al. (1993). *Nucl. Acids Res.* 21:3537–3544.
Hiratsuka et al. (1989). *Mol. Gen. Genet.* 217:185–194.
Helentjaris et al. (1985). *J Plant Mol. Biol.* 5:109.
Horikawa, Y. et al. (1993). *Res. Bull. Obihiro University Natural Science* 18:143–146.
Innis, et al. (1990). *PCR Protocols: A Guide to Methods and Applications* (Academic Press, San Diego, Calif.).
Jablonski, E., et al. (1986). *Nucl. Acids Res.* 14:6115–6128.
Janke, A. et al. (1997). *Proc. Natl. Acad. Sci. USA* 94:1276–1281.
Jeffreys et al. (1985). *Nature* 316:76.
Johnston et al. (1988). *Science* 240:1538–1541.
Khan et al. (1996). *Transgenic Res.* 5:179–185.
Korab-Laskowska, M. et al. (1998). *Nucl. Acids Res.* 26:138–144.
Kubo, T., et al. (1988). *FEBS Letts.* 241:119.
Landry et al. (1985). *Plant Mol. Biol. Rept.* 3:174.
Landegren, et al. (1988). *Science* 242:229.
Lopez, S. V. et al (1996). *Genomics* 33:229–246.
Maniatis, T. et al. (1982). *Molecular Cloning: A Laboratory Manual* (Cold Spring Harbor Laboratory, Cold Spring Harbor, N.Y.).
Maier, R. M., et al. (1995). *J. Mol. Biol.* 251:614–628.
Maliga, P. (1993). *In Methods in Plant Molecular Biology: A Laboratory Manual*, (eds. Maliga et al., Cold Spring Harbor Laboratory, Cold Spring Harbor, N.Y.).
Martin, R., et al. (1990). *Bio Techniques* 9:762–768.
Matthews and Kricka (1988). *Anal. Biochem.* 169:1.
McKersie et al. (1993). *Plant Physiol.* 103:1155–1163.
Murashige et al. (1962). *Plant Physiol.* 15:493497.
Nguyen, Q., et al. (1992). *Bio Techniques* 13:116–123.
Nielsen et al. (1985). In *Isozymes: Current Topics in Biol. Med. Res.*, Vol. 12, Rattazzii et al., eds., Alan R. Liss, Inc., New York, pp. 1–32.
Ohyama et al. (1986). *Nature* 322:572–574.
Poerba, Y. S. et al. (1997). *Crop Science* 37:1302–1305.
Rigby, P. W. J., et al. (1977). *J. Mol. Biol.* 113:237–251.
Roe, B. A. et al. (1985). *J. Biol. Chem.* 260:9759–9774.
Sambrook, J., et al. (1989). *Molecular Cloning: A Laboratory Manual*, 2nd Ed. (Cold Spring Harbor Laboratory, Cold Spring Harbor, N.Y.).
Shields et al. (1983). In *Isozymes in Plant Genetics and Breeding*, Part A, Tanksley et al., eds., Elsevier Science Publishers, Amersterdam, pp. 443–468.
Shinozaki et al. (1986). *The EMBO J.* 5:2043–2049.
Spargo, C. A., et al. (1996). *Mol. Cell. Probes* 10:247–256.
Staub et al. (1992). *The Plant Cell* 4:3945.
Svab and Maliga (1993). *Proc. Natl. Acad. Sci. USA* 90:913–917
Svab et al. (1990). *Proc. Natl. Acad. Sci. USA* 87:8526–8530.
Unseld, M. et al. (1997). *Nature Genetics* 15:57–61.
Wakasugi, T. et al. (1997). *Proc. Natl. Acad. Sci. USA* 94:5967–5972.
Walker, G. T., et al. (1992). *Nucl. Acids Res.* 20:1691–1696.
Wolff, G. et al. (1994). *J. Mol. Biol.* 237:75–86.
Wu, et al. (1989). *Genomics* 4:560–569.
Zhou, Y. H. et al. (1995). *Plant Mol. Biol.* 28:635–646.
EP 225,807A
EP 320,308A
U.S. Pat. No. 4,683,195
U.S. Pat. No. 4,683,202
U.S. Pat. No. 4,868,105
U.S. Pat. No. 4,963,663
U.S. Pat. No. 5,004,863
U.S. Pat. No. 5,015,580
U.S. Pat. No. 5,024,944
U.S. Pat. No. 5,159,135
U.S. Pat. No. 5,175,385
U.S. Pat. No. 5,177,010
U.S. Pat. No. 5,187,073
U.S. Pat. No. 5,188,958
U.S. Pat. No. 5,270,184
U.S. Pat. No. 5,324,646
U.S. Pat. No. 5,350,689
U.S. Pat. No. 5,409,818
U.S. Pat. No. 5,416,011
U.S. Pat. No. 5,451,513
U.S. Pat. No. 5,455,166
U.S. Pat. No. 5,476.995
U.S. Pat. No. 5,484,956
U.S. Pat. No. 5,489,520
U.S. Pat. No. 5,489,742
U.S. Pat. No. 5,510,523
U.S. Pat. No. 5,530,192
U.S. Pat. No. 5,545,817
U.S. Pat. No. 5,545,818
U.S. Pat. No. 5,563,055
U.S. Pat. No. 5,569,829
U.S. Pat. No. 5,569,831
U.S. Pat. No. 5,573,933
U.S. Pat. No. 5,576,198
U.S. Pat. No. 5,589,604
U.S. Pat. No. 5,589,612
U.S. Pat. No. 5,589,617
U.S. Pat. No. 5,597,718
U.S. Pat. No. 5,610,042
U.S. Pat. No. 5,631,152
U.S. Pat. No. 5,641,664
U.S. Pat. No. 5,674,687.
U.S. Pat. No. 5,679,558
U.S. Pat. No. 5,723,764
U.S. Pat. No. 5,736,627
U.S. Pat. No. 5,736,369
U.S. Pat. No. 5,741,957.

What is claimed is:

1. Plant germplasm comprising cells having a transgenic organelle, said transgenic organelle comprising a heterologous identifier nucleotide sequence integrated into the transgenic organelle's genome, wherein said sequence is not capable of being expressed in the germplasm, and said plant is selected from the group consisting of alfalfa, red clover, orchardgrass, tall fescue, timothy and sudangrass.

2. Germplasm comprising cells having a transgenic organelle, said transgenic organelle comprising a heterologous identifier nucleotide sequence integrated into the transgenic organelle's genome, wherein said germplasm is a non-human animal.

3. Plant cells having a transgenic organelle, said transgenic organelle comprising a heterologous identifier nucleotide sequence integrated into the transgenic organelle wherein said sequence is not capable of being expressed in the germplasm and said plant is selected from the group consisting of alfalfa, red clover, orchardgrass, tall fescue, timothy and sudangrass.

4. Cells having a transgenic organelle, said transgenic organelle comprising a heterologous identifier nucleotide sequence integrated into the transgenic organelle's genome, wherein said cells are non-human animal cells.

5. A method for identifying a parent of plant germplasm suspected of being progeny of a first germplasm which contains plant cells having a transgenic organelle comprising a heterologous identifier nucleotide sequence integrated into the organelle genome, said method comprises: a) isolating DNA from said suspected germplasm; and b) determining the presence of said identifier nucleotide sequence in said DNA, wherein the presence of said identifier nucleotide sequence in said DNA identifies the first germplasm as a parent of the suspected germplasm, and wherein said sequence is not capable of being expressed in the germplasm and said plant is selected from the group consisting of alfalfa, red clover, orchardgrass, tall fescue, timothy and sudangrass.

6. A method for identifying a parent of germplasm suspected of being progeny of a first germplasm which contains cells having a transgenic organelle comprising a heterologous identifier nucleotide sequence integrated into the organelle genome, said method comprises: a) isolating DNA from said suspected germplasm; and b) determining the presence of said identifier nucleotide sequence in said DNA, wherein the presence of said identifier nucleotide sequence in said DNA identifies the first germplasm as a parent of the suspected germplasm and wherein said germplasm is a non-human animal.

* * * * *

SEQUENCE LISTING

<160> NUMBER OF SEQ ID NOS: 1

<210> SEQ ID NO 1
<211> LENGTH: 1131
<212> TYPE: DNA
<213> ORGANISM: Unknown Organism
<220> FEATURE:
<223> OTHER INFORMATION: Description of Unknown Organism:chicken

<400> SEQUENCE: 1

```
atggcagatg aggaaattgc tgccctggtg gtggacaatg gctctggtat gtgcaaggca      60
ggctttgctg gggatgatgc ccctagggct gtgttccctt ccattgtggg acgccccgg      120 catcaaggtg tcatggtggg tatggggcag aaggacagct atgtgggaga cgaagcccag     180
agcaagaggg gaatcctcac cctgaagtat cctattgagc atggcattgt caccaactgg     240
gatgacatgg agaagatctg gcaccacacc ttctacaatg agttgcgtgt tgctccagag     300
gagcaccctg tcctgcttac tgaggccccg ctgaaccc ta aagccaacag ggagaagatg     360
acccagatca tgtttgagac cttcaacact ccagctatgt acgtggccat ccaggctgtg     420
ctgtcccttt atgcctctgg tcgcaccacc ggcatcgtca tggactctgg ggatggtgtc     480
acccacacag tgcccattta cgagggctat gctctgcccc atgccatcct gcgtctggac     540
ttggctggcc gtgacctgac tgactacctc atgaagatcc taacagagcg aggttatagc     600
ttcaccacca cggctgagag ggagattgtc cgtgatatca aggaaaagct gtgctatgtt     660
gctctagact ttgagcagga gatggcaacg gctgcctcat cctcctccct agagaaaagc     720
tatgagctgc cggatgggca ggtgatcacc attgggaatg agcgcttccg atgccccgag     780
gccatcttcc aaccttcctt cttgggcatg gagtcctgcg gcatccacga gaccaccttc     840
aactccatca tgaagtgtga tgtggacatc aggaaggacc tgtatgccaa caccgtgctg     900
tctgggggta ccaccatgta ccctggcatc gctgacagga tgcagaagga gatcacagcg     960
ctagcaccca gcaccatgaa gatcaagatc atcgcccc ac cggagcgcaa gtattctgtc    1020
tggattggtg gctccatcct agcctccctc tccaccttcc agcagatgtg gatcagcaag    1080
caggagtatg atgagtctgg cccctccata gtccatcgca agtgcttcta g             1131
```